(12) United States Patent
Suter et al.

(10) Patent No.: US 9,039,413 B2
(45) Date of Patent: May 26, 2015

(54) DENTAL TOOLS FOR GUIDED SURGERY

(75) Inventors: Edmund Suter, Niederdorf (CH);
Stephane Courvoisier, Colombier (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 12/969,055

(22) Filed: Dec. 15, 2010

(65) Prior Publication Data

US 2011/0177469 A1    Jul. 21, 2011

(30) Foreign Application Priority Data

Dec. 17, 2009  (EP) ..................................... 09015587

(51) Int. Cl.
| | | |
|---|---|---|
| A61C 3/00 | (2006.01) | |
| A61C 8/00 | (2006.01) | |
| A61B 19/00 | (2006.01) | |
| A61C 1/08 | (2006.01) | |

(52) U.S. Cl.
CPC .............. *A61C 8/0089* (2013.01); *A61B 19/201* (2013.01); *A61B 2019/462* (2013.01); *A61B 2019/5437* (2013.01); *A61C 1/084* (2013.01)

(58) Field of Classification Search
CPC ................. A61B 2019/462; A61B 2019/5437; A61C 1/084; A61C 8/0089; A61C 19/04
USPC ................ 433/75, 144, 165, 220; 606/80, 96; 408/80, 202, 110; 29/896; 206/572
See application file for complete search history.

(56) References Cited

U.S. PATENT DOCUMENTS

| | | | | |
|---|---|---|---|---|
| 3,576,076 A | * | 4/1971 | Weissman ..................... | 433/165 |
| 4,393,539 A | * | 7/1983 | Weissman ....................... | 16/426 |
| 5,741,267 A | * | 4/1998 | Jorneus et al. ................ | 606/102 |
| 5,890,897 A | * | 4/1999 | Kruger et al. ................... | 433/75 |
| 6,213,771 B1 | * | 4/2001 | Fischer ........................... | 433/75 |
| 6,863,529 B2 | * | 3/2005 | Strong et al. .................. | 433/165 |
| 7,048,477 B2 | * | 5/2006 | Abrams ....................... | 408/1 R |
| 7,771,143 B2 | * | 8/2010 | Bharadwaj et al. ........... | 408/1 R |
| 7,960,011 B2 | * | 6/2011 | Sahlberg et al. .............. | 428/172 |
| 2002/0172923 A1 | * | 11/2002 | Strong et al. .................. | 433/165 |
| 2005/0026114 A1 | * | 2/2005 | Nilo et al. ..................... | 433/173 |
| 2006/0008771 A1 | * | 1/2006 | Courvoisier .................. | 433/165 |
| 2006/0147879 A1 | * | 7/2006 | Mueller ..................... | 433/165 |
| 2006/0204929 A1 | * | 9/2006 | Kitamura et al. ............. | 433/173 |

(Continued)

FOREIGN PATENT DOCUMENTS

| | | |
|---|---|---|
| EP | 2 060 240 A2 | 5/2009 |
| WO | WO 2007/129955 A1 | 11/2007 |
| WO | WO 2008/149822 A1 | 12/2008 |

OTHER PUBLICATIONS

Biomet 3i (Navigator TM System for CT Guided Surgery Manual at www.biomet3i.com).*

(Continued)

*Primary Examiner* — Cris L Rodriguez
*Assistant Examiner* — Mirayda A Aponte
(74) *Attorney, Agent, or Firm* — Novak Druce Connolly Bove + Quigg LLP

(57) ABSTRACT

Surgical tool for use in guided surgery having a distal end portion having a functional element, a shank on the opposite end of the tool, and a substantially circular cylindrical guide portion. The guide portion is located between the functional element and the shank and has at least one visual marker. The at least one marker has at least one recess which is finite in the circumferential direction such that, at the axial location of the recess a section of guide portion having outer radius r is maintained.

19 Claims, 5 Drawing Sheets

(56) References Cited

U.S. PATENT DOCUMENTS

| | | | |
|---|---|---|---|
| 2006/0286506 A1* | 12/2006 | Birnholtz | 433/165 |
| 2007/0206996 A1* | 9/2007 | Bharadwaj et al. | 408/202 |
| 2007/0298376 A1* | 12/2007 | Kmiecz et al. | 433/165 |
| 2009/0130630 A1 | 5/2009 | Suttin et al. | |
| 2009/0298009 A1* | 12/2009 | Brajnovic | 433/75 |
| 2010/0047737 A1* | 2/2010 | Richard | 433/75 |
| 2011/0053112 A1* | 3/2011 | Weissman | 433/165 |
| 2011/0256500 A1* | 10/2011 | Crudo | 433/75 |
| 2012/0009543 A1* | 1/2012 | Meier et al. | 433/165 |
| 2012/0129126 A1* | 5/2012 | Nouriam et al. | 433/75 |

OTHER PUBLICATIONS

Art1021A Navigator Manual at www.biomet3i.com, RevA on Oct. 2007.*

ART1019 Clinical Perspectives at www.biomet3i.com, RevA on Oct. 2007.*

Biomet 3i—Navigator TM System for CT Guided Surgery Manual, Rev. A Oct. 2007—www.biomet3i.com.*

May 27, 2010 EP Search Report and Written Opinion in related Application No. EP 09 015 587.0.

* cited by examiner

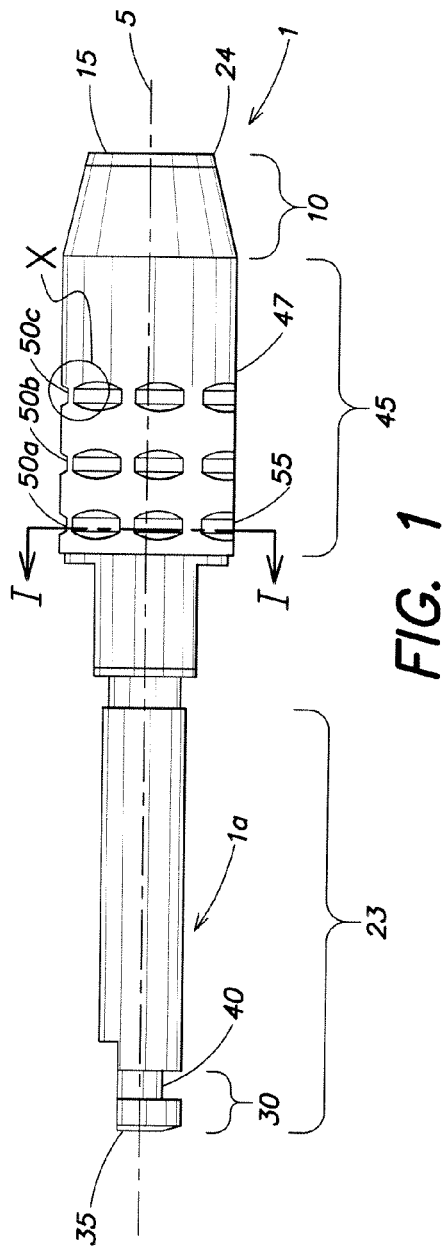
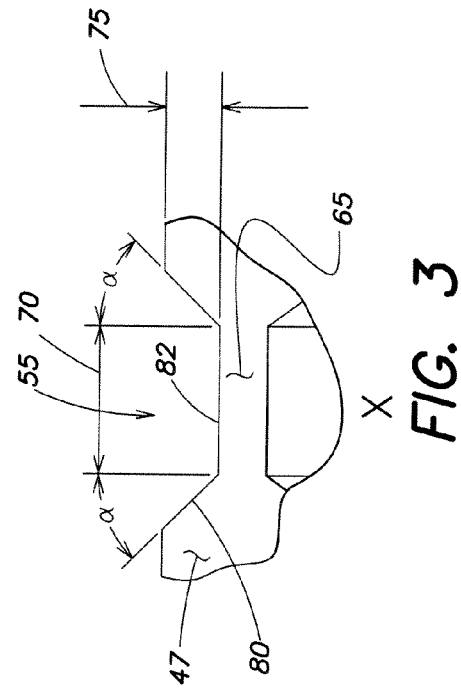
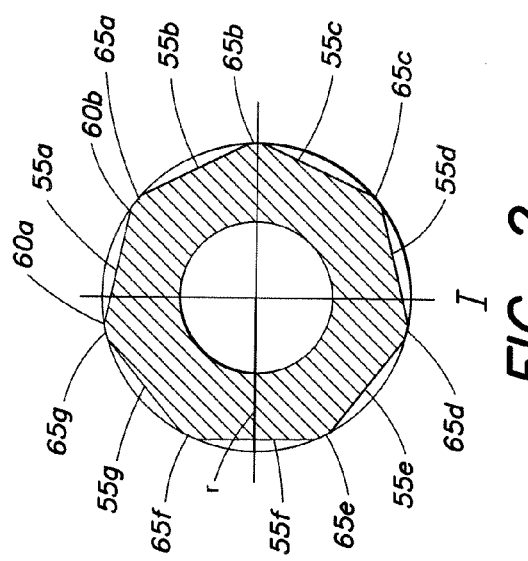

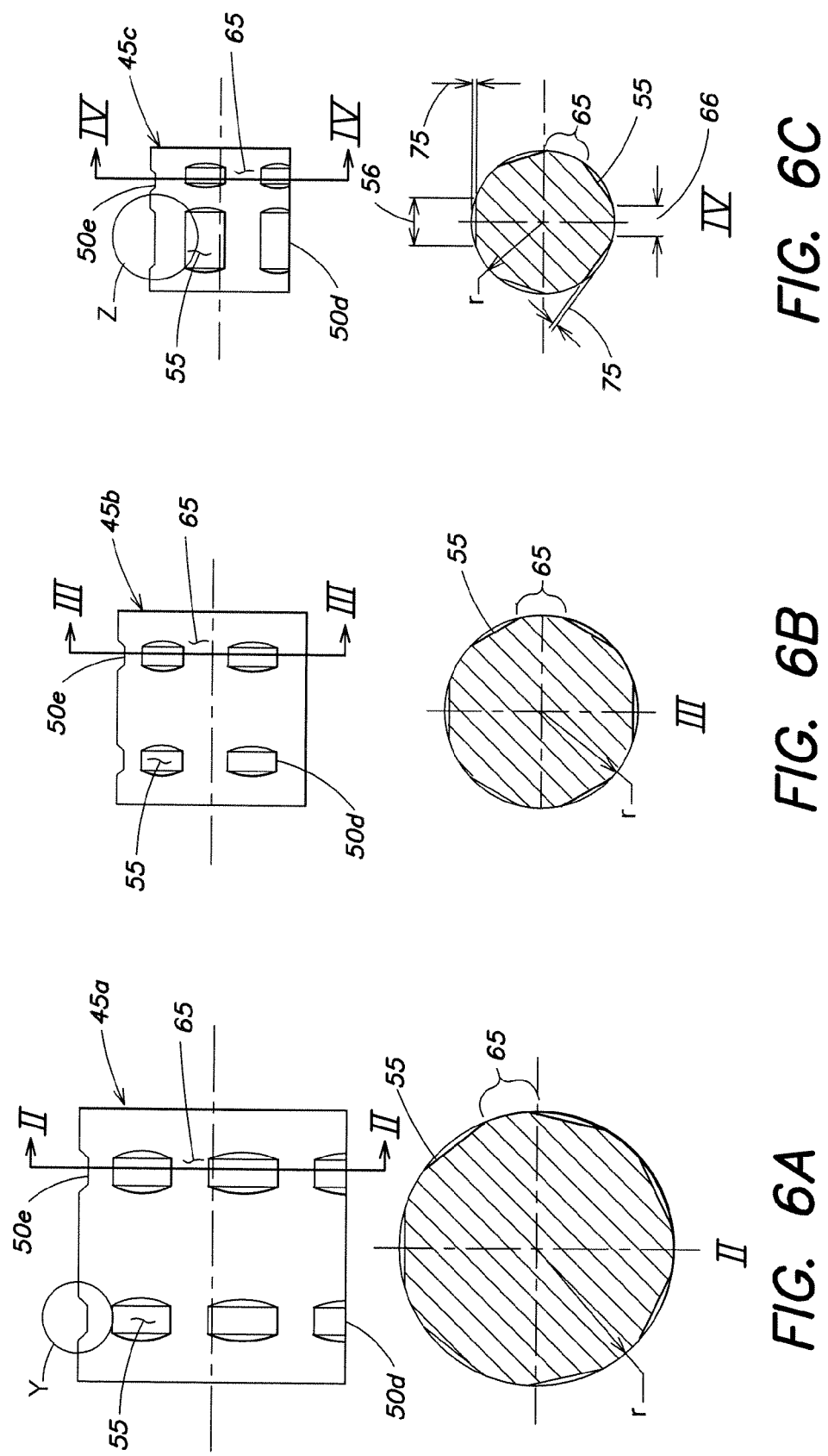

DENTAL TOOLS FOR GUIDED SURGERY

FIELD OF THE INVENTION

The present invention relates to a dental surgical tool comprising a guide portion for use in guided surgery.

In order to place a dental implant within the mouth of a patient, a suitable cavity must be created within the patient's jaw bone. This cavity must be of the correct depth and diameter, and be correctly positioned and orientated. This is crucial in order to ensure that the implant does not interfere with existing teeth, nerve bundles and/or implants and also to give good stability and an aligned and aesthetically pleasing end result.

BACKGROUND

The availability of computer tomography and specialised computer software allows for detailed pre-operative planning, during which the precise location and dimensions of the required cavity in a patient's jaw bone can be virtually modelled. Based on this model, a template specific to each patient can be designed and manufactured, which can be placed over the patient's teeth, gums or bone. This template contains one or more guide channels precisely positioned along the axis of the bone cavities to be drilled. During their use, all surgical tools required for creating the cavity and guiding the implant are inserted through this guide channel to ensure the correct alignment of the tools and implant with respect to the bone. This necessitates a close fit between the guide channel and the body of each tool. So that the guide channel can accurately guide tools having a smaller diameter than the channel, a series of guide channel collars can be provided. These are placed over and/or in the guide channel and effectively reduce its diameter to correspond to the tool in use. A surgical procedure with some kind of guide element, for example the template and collars described above, is herein referred to as guided surgery.

The precise guidance of surgical tools is very important during all steps of guided surgery. The use of a template constitutes a great facilitation with respect to correct positioning and alignment of the implant and for precise handling of the tools. In addition, it can also be used to assist in the control of tool and implant insertion depth.

Depth control can be achieved via physical or visual means, or a combination of both. The type used will depend on user preference but is also influenced by tool function.

During drilling, for instance, depth information is crucial in order to precisely control the depth of the drill head. This avoids damaging, e.g. of underlying nerves and other anatomical structures. For this reason, a physical stop is often provided to prevent over-drilling. For example, the drill body can undergo a step increase in diameter at a certain distance from the drill tip. This portion of increased diameter can not pass through the guide channel and therefore will limit the axial feed of the drill. In addition specific tools have been developed to limit the axial feed of drilling devices during implant bed preparation. These tools can be applied with or without the aid of a template.

WO 2006/062459 describes a dental drill device to which sleeves of different lengths can be attached. Towards the drill head, the sleeves have bearing surfaces, which, in cooperation with the bone, template or other guide element, can be used to limit the drill length or the drill depth.

In addition, or alternatively, visual indicators can be provided on the drill head or body to inform the surgeon how deep the drill has penetrated.

By providing tools with only visual depth indicators the flexibility available to the dentist or surgeon is increased, as the tool or implant may be inserted to a deeper depth than initially planned.

Such visual indications are particularly useful for steps which do not require meticulous depth control, during flattening of the alveolar ridge with a milling cutter, for example, or removing mucosa with a punch. In such cases, sophisticated technical features to precisely determine the position of the functional element of the tool or the use of physical stops are not necessary.

Physical stops are also not always desirable from an operative viewpoint. For example, a tap is used in dentistry to cut threads into the bone cavity walls. Said threads possess a pitch equal to that of the implant to be inserted. If the tap is brought to a sudden vertical stop whilst continuing to rotate, the threads created within the implant hole will be destroyed. The same problem exists in respect of the implants themselves, which are inserted into the cavity using a transfer piece or implant post.

In this context, tools for use in guided surgery have been developed that cooperate with the template or other guide element to provide visual information on insertion depth. These tools comprise a guide portion, which, while in use, is in contact with the guide element. Said guide portion features one or several marks at defined distances from a reference point of the functional element, for example the tool tip or the start of the cutting edge. These marks, together with the template or other guide element, help the practitioner to ascertain the axial feed of the tool.

Laser-marking is a known method of providing tools with visual marks. These marks are created at one or more set distances from the functional element of the tool. During the process of laser-marking, the irradiated material melts and the corresponding surface of the tool slightly deforms. This deformation results in a slight increase in diameter of a cylindrical tool. The amount of deformation is dependent on the energy used during the laser-marking process, however typically this is greater than 0.01 mm. Due to the close fit of the tool with the guide channel, said diameter increase can prevent smooth guidance of the tool. Additionally, due to the rotation and axial movement of the tool during usage, the laser marks are quickly abraded. As a result thereof, the practitioner's ability to track the axial feed of the tool is diminished. Similar problems are experienced with other forms of marking, e.g. painting etc.

SUMMARY OF THE INVENTION

It is therefore a problem addressed by the present invention to improve the outlined features of existing surgical tools. Specifically, the invention aims to prevent abrasion of the marks during usage, cleaning or sterilisation to ensure good readability even after multiple employments, and obtain smooth guidance of the guide portion when inserted in the guide channel.

The surgical tool according to the present invention for use in guided surgery with a longitudinal axis comprises a distal end portion having a functional element, a shank on the opposite end of the tool and a cylindrical guide portion having an outer radius r which defines a guide surface for cooperation with a guide element, the guide portion being located on the longitudinal axis between the functional element and the shank and having at least one marker, the at least one marker comprising at least one recess, said at least one recess being finite in the circumferential direction such that, at the axial location of the recess, a section of guide surface is maintained. Said at least one marker is preferably a visual marker, that is a marker, which can be detected by the human eye.

It has been found that a surgical tool according to the present invention provides a durable visual marking whilst still ensuring a tight fit between the guide element and the surgical tool, and therefore the visual marking does not adversely affect the guidance provided by the element. Due to the at least one finite recess it is possible to provide a tool with a visual depth guide, which has a long life time and a high accuracy.

The at least one recess in the guide portion acts as a visual marker to the user, e.g. of the distance to the tip of the functional element. As this recess is located within the outer radius r of the guide portion it is not abraded during the use of the tool. A continuous recess, stretching 360° about the guide portion, could result in the tool catching on the guide element, thus affecting the smooth insertion and removal of the tool. Further, it is possible that a continuous recess would result in the tool entering the drill site at a slight angle, thus affecting the precision of the guided surgery. This is prevented in the present invention by the provision of a recess which is finite in length. This ensures that, at the axial location of the visual marker, there remains a section of the guide portion with outer radius r, to enable correct guiding of the tool.

The term "surgical tool" in relation to the present invention refers to tools or instruments which a physician or practitioner may use during any kind of surgical procedure, including dental surgical procedures, such as implantation of dental implants. The surgical tool according to the present invention comprises a longitudinal axis and, on a distal end portion of the surgical tool, a functional element. This functional, or operative, element is arranged to carry out the tool's function. The functional element may operate, for example, as a punch, a milling cutter, a tap, a drill, a profile drill, a transfer piece or may fulfil any other function of a dental and/or surgical tool. The tool further has, opposite to the functional element along the longitudinal axis, a shank. The term "shank" is used to signify a connecting part which enables attachment of the surgical tool to a drive tool, such as a ratchet or drill handpiece. The shank is not limited to any particular physical shape and can take any desired form. In between and distinct from these two end portions is the guide portion, which is positioned such that, in use, it can co-operate with a guide element.

The term "guide element" is intended to cover any element which provides positional guidance to a surgical tool in order to define the correct incidence angle of the tool with respect to the patient during surgery, via direct sliding contact between the guide portion and the guide element. Typically a guide element defines, either alone or in combination with a second guide element, a guide channel. The guide channel can be open or closed, i.e. it does not have to surround the tool completely. The guide channel is arranged for sliding contact with the tool during surgical use, i.e. the guide element and tool are not fixedly connected. Templates are a particularly preferred form of guide element, and can be used in combination with additional guide elements, such as guide collars etc, to create or modify a guide channel for the surgical tool.

The guide portion of the surgical tool has a substantially cylindrical shape with an outer, guide, surface defined by radius r. The guide channel has a shape complementary to the outer surface of the guide portion such when the guide portion is inserted within the guide channel and rotated about its longitudinal axis, contact between the guide surface and channel is maintained and any change in orientation of the longitudinal axis is prevented, in order to ensure precise guidance of the tool. Although the guide portion is normally an integral part of the tool, it is also possible for the guide portion to comprise a separate element which is fixedly attached to the tool during use.

Traditionally the guide portion would comprise a smooth, continuous guide surface. The guide portion of the surgical tool according to the present invention however comprises one or more visual markers, each marker consisting of at least one finite recess. A recess in the context of the present invention means a segment of the guide portion having a radius less that the outer radius r. In this way the surface of the recess is not brought into sliding or rotational contact with the guide element during use. However, as the recess is finite in the circumferential direction a section of guide surface is maintained at every axial location of the guide portion. This ensures that the guidance provided by the guide portion is not compromised by the visual markers.

Each marker can comprise one or several recesses. In a preferred embodiment, the at least one visual marker comprises a plurality of finite recesses, separated from each other in the circumferential direction by sections of guide surface. This increases the visibility of the marker as well as the precision of the guidance. The recesses in a single marker can vary in terms of length and shape, however preferably the recesses are uniform.

In a preferred embodiment, the plurality of recesses lie in the same axial plane and, therefore, have the same distance to the distal end portion of the tool. The recesses can therefore be used to indicate to the user the distance from a defined point of the functional element, e.g. the tip. It is possible for the visual markers to directly indicate the penetration depth of the tool, i.e. in order to drill to a predetermined depth the user inserts the tool into the bone until the visual marker is level with the bone surface. However, it is often hard for the surgeon to obtain a clear view of the drill site, due to bone chips, blood, mucosa etc. In addition during guided surgery the template or other guide element can obscure the drill site.

Therefore it is preferable for the at least one visual marker to be positioned such that it provides a depth gauge in combination with the guide element, i.e. the template, collar or other guide element acts as a reference point. In this way, when the visual marker is level with a defined point of the guide element, e.g. the upper surface of the guide element, the user knows that the tool has reached a particular depth. The visual markers can hence be used to control movements of the tool in the axial direction relative to the guide element during the course of the implantation procedure. With the aid of the recesses in the immediate vicinity of the template, the practitioner is able to follow a small axial feed, for example, of a milling cutter during the process of flattening the bone surface.

Preferably the plurality of recesses in a single visual marker are positioned in such a way that at least one recess is visible from any viewing angle. However, the precise number and shape of recesses will be determined in part by the standard operating conditions of the tool. For example, if a tool will normally be used at a high rotational speed, e.g. a drill or milling cutter, the recesses can be spaced further apart than on a tool which will normally be used at much lower speeds, e.g. a tap or transfer piece, which are often rotated manually or with a ratchet.

Regarding the number and spacing of recesses, the circumferential length of the individual recesses, and the circumferential length of the remaining guide surface segments, the following issues should be taken into account: On one hand, recesses which are clearly visible during the operating conditions of the tool are desired and, on the other hand, the remaining segments of the guide portion need to be sufficient in number and length in order to provide accurate and smooth guidance in cooperation with the guide element. Depending on the type and size of tool a skilled man can design the visual markers in order to ensure these two requirements are met.

A typical guide portion has a diameter of between 3 and 7 mm, preferably 5 mm. Preferably, the ratio ($L_R/L_G$) between the combined recess length of a marker ($L_R$) and the combined length of the remaining segments of the guide surface in the same axial plane ($L_G$) is between 1 and 3, preferably between 1.4 to 2.7. The optimum number of recesses per set is 1 to 9, which are preferably evenly spaced in the circumferential direction.

Preferably, the guide portion includes a plurality of visual markers lying in different axial planes. Preferably, the guide portion comprises between 1 and 5 separate visual markers, however this number can vary depending on the tool type. Said visual markers are preferably evenly spaced in the axial direction. However, it is also possible that the distance between two visual markers increases towards the functional element, since depth control is more important at the end of the application than at the beginning, that is after deeper insertion of the tool into the guide channel of the template or other guide element.

Preferably, the at least one recess contains a mark. This provides the recess(es) with a contrasting colour or visual nature with respect to the tool body or guide portion. The marks are preferably produced by laser-marking, but any kind of marking can be used, for example, a non-toxic paint or dye could be applied to the surface of the recess, or they could be sandblasted.

Said mark is contained within the recess, and, as a result, the guide portion of the tool according to the present invention allows smooth guidance with the guide element, despite the mark.

Furthermore, the mark is safe from any abrasion during usage. This fact extends the readability of the mark and, consequently, the life time of the tool. The depth of the at least one recess is preferably between 0.03 and 0.5 mm, most preferably 0.1 mm. The depth must in any event be deep enough to ensure that the contour of the mark lies completely within the guide surface defined by the outer radius r of the guide portion.

The at least one recess can be any suitable shape. For example, the recesses may be circular indents, cut outs having a rhombus, rectangular or other polygonal shape etc. Preferred shapes are those having a linear edge running perpendicular to the longitudinal axis of the tool as this provides a clear reference line for the user.

This is particularly beneficial when the visual markers are to be used to control the depth of the tool during use. Preferably the at least one recess comprises a finite groove. By groove it is meant a channel-like recess in the lateral area of the guide portion extending in the circumferential direction.

The groove is preferably formed via machining, e.g. drill cutting, profile milling etc. Other preferred production methods are laser cutting and wire eroding (electrical discharge machining). The finite groove can adopt any shape, for example this may have a parabolic or V-shaped cross section. In a preferred embodiment however, the at least one groove comprises two sides and a ground, which is preferably planar. The sides can be bevelled at an angle α. The planar ground and the bevelled sides both contribute to greater visibility, however too great a bevelled side creates a large surface area and can lead to confusion as to the precise location of the visual marker. Therefore the bevelled sides are preferably at an angle α of between 0° and 45°. In this preferred embodiment a mark can be formed on the ground of the at least one groove. Preferably the grounds of the grooves are laser-marked.

The axial width of the recess is preferably between 0.4 and 2.5 mm, more preferably between 0.5 and 2.0 mm. When a surgical tool comprises a plurality of visual markers it is possible for the recesses of each marker to have the same or different axial widths. Recesses having a relatively large axial width, e.g. 1 or 2 mm, can act as a "double depth indicator". This means that, when the reference point of the guide element is level with the most distal end of the recess the user knows the tool is at a first defined depth, e.g. 8 mm, whereas when the guide element is level with the opposing end of the recess the user knows that a second predefined depth has been reached, e.g. 10 mm.

The tool according to the present invention can be any tool for use in guided dental surgery and is preferably a punch, a milling cutter, a drill, a tap, a profile drill or a transfer piece.

In a preferred embodiment, the tool according to the present invention is a mucosa punch. This tool is specific for use in guided surgery. Conventional implantation procedure includes cutting the mucosa around the implant site as a first surgical step. Then the mucosa is pulled back from the bone to expose the drilling site and quite a large section of the surrounding alveolar bone. Using guided surgery, it is sometimes not necessary to pull a large section of mucosa back from the bone. Instead, only the mucosa covering the designated drill site needs to be removed. This task can be done with the aid of the mucosa punch. The functional element of said punch is a hollow end portion with a circumferential cutting edge.

Possible guide elements for the use in connection with the tool according to the present invention are guide collars such as conventional drill handles or "C-handles" as described in EP 08 021 712, for instance. They can be used in combination with a template. With their help, for example, the diameter of the guide channel can be adjusted to match the diameter of the guide portion of a specific tool. Said guide elements may be sold together with the tool according to the present invention in a kit.

Although the visual marker of the present invention has so far been described in connection with providing a depth guide, these markers could equally be used to indicate other qualities, for example, tool width or function. For instance, tools having the same functional element but different diameters may be distinguished from one another by providing each tool with recesses of different axial widths, recesses having differently coloured marks or a different number of markers. A set of tools provided in three diameters could be distinguished from one another by providing, on the tool having the smallest diameter a single visual marker in the form of a dashed line, on the tool having the middle diameter visual markers creating two dashed lines, and on the tool of largest diameter visual markers forming three dashed lines. Once again, the visual markers have the advantages of providing a long lasting visual mark without compromising the precision of the tool guidance system.

Of course, it is possible to provide a range of visual markers on the same tool, some designed to indicate depth and others relating to other properties.

BRIEF DESCRIPTION OF THE FIGURES

Preferred embodiments of the present invention will now be described, by way of example only, with reference to the accompanying drawings, in which:

FIG. 1 shows a side view of a mucosa punch in accordance with the present invention;

FIG. 2 shows a cross section along line (I)-(I) of FIG. 1;

FIG. 3 shows detail (X) of FIG. 1;

FIGS. 6A-6C show views of guide portions of different diameters, FIG. 6A showing a first embodiment with a cross section taken along line (II)-(II), FIG. 6B showing another embodiment with a cross section taken along line (III)-(III) and FIG. 6C showing yet another embodiment with a cross section taken along line (IV)-(IV).

DETAIL DESCRIPTION

Figure 4:
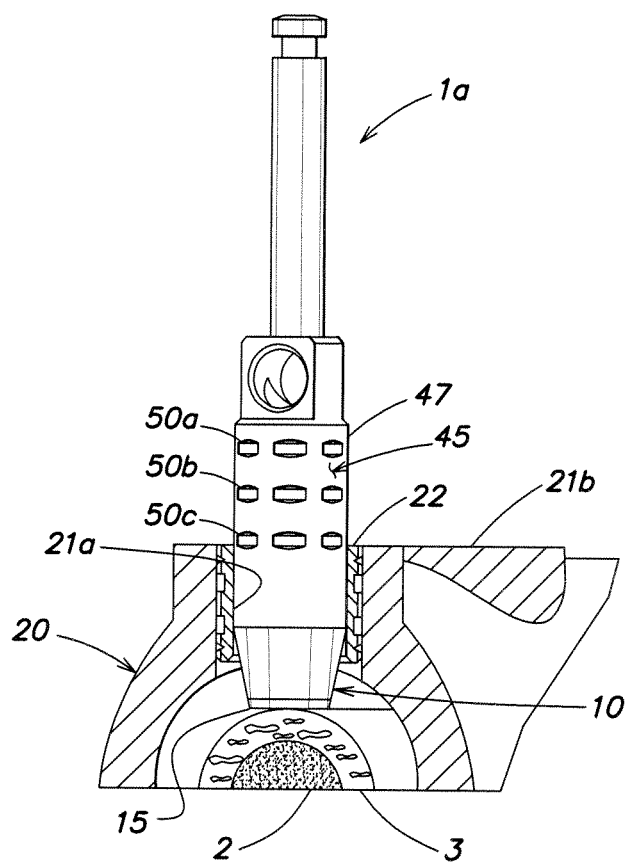
FIG. 4 shows a schematic view of the mucosa punch of FIG. 1 in use.

FIG. 1 shows a first illustrative embodiment of a tool 1 according to the present invention in the form of a mucosa punch 1a. The punch 1a comprises a longitudinal axis 5. The punch 1a has at one end, that is the distal end, a functional element 10 in the form of a truncated hollow cone having a cutting edge 15 at the tip 24. Said cutting edge 15 is intended for cutting the mucosa prior to drilling in the bone tissue. At the opposite end, the punch 1a has a shank part 23 with an exposed connection area 30. The connection area 30 is intended to be received in a generally known drill holder device and has a rotation-preventing means 35, and an axial securing means 40. The rotation-preventing means 35 and the axial securing means 40 allow for the mucosa punch 1a to be brought into a fixed connection with the drill holder device, which, for example, is part of a drill drive or a hand drill.

The punch 1a comprises a substantially circular cylindrical guide portion 45 with a radius r (see FIG. 2) located on the longitudinal axis 5 between the functional element 10 and the shank 23. The lateral area of the guide portion 45 forms a guide surface 47.

Guide portion 45 has three visual markers 50a, 50b, 50c. These markers 50a, 50b, 50c are spaced apart from one another in the axial direction. In this embodiment, the distance between the first visual marker 50a and the second visual marker 50b is the same as the distance between the second visual marker 50b and the third visual marker 50c. However, depending on the medical application, it would also be possible to have only two markers or more than three markers, and the distances between the visual markers could increase towards the functional element 10, since the depth control is more important at the end of the application than at the beginning. Visual markers 50a, 50b, 50c are each formed by a series of finite recesses in the form of grooves 55 extending in the circumferential direction. This creates a "dashed line" effect around the guide portion 45, with the finite grooves 55 being separated from one another by sections of guide surface 47. In the axial direction, all the grooves 55 have the same width 70 and, in the circumferential direction, they have the same length 56.

FIG. 2 shows a cross section along the line (I)-(I) in FIG. 1 and reveals seven grooves 55a-55g with planar grounds 82 (see FIG. 3). Each of these grooves 55 is finite. Groove 55a, for example, has two ends 60a and 60b. The same applies to the other grooves 55b-55g accordingly. The remaining segments 65a-65g in between the seven finite grooves 55a-55g have outer radius r and thus form part of the guide surface 47. After insertion of the guide portion 45 into the guide channel, the remaining segments 65a-65g allow smooth and accurate guidance of the punch 1a along its longitudinal axis 5. Of course, other numbers of grooves 55 per visual marker 50 are also possible and the optimal number depends on the radius r of the guide portion 45.

FIG. 3 shows a detail X, which shows one groove 55 of visual marker 50c with a width 70 in the axial direction, with a groove depth 75 and with a ground 82. Groove depth 75 is deep enough to ensure that any mark applied to ground 82 lies completely within the outer radius r of the guide portion 45. This enables a smooth guidance despite the marks. The sides 80 of the groove can be bevelled at an angle α, wherein said angle α is preferably between 0° and 45°.

FIG. 4 shows the mucosa punch 1a of FIG. 1 in use, in cooperation with a template 20. The template 20 for use with the tool 1 is shaped to securely fit over the patient's teeth, gums or bone. In this example, the template is shown positioned over the edentulous jaw of a patient. Alveolar bone 2 is covered by soft tissue (mucosa) layer 3. The template 20 comprises a number of guide channels 21a, 21b, the axes of which are aligned with the desired axes of the bone cavities to be drilled. In this embodiment, channel 21a comprises a protective metal sleeve 22 which protects the template 20 from the heat and abrasion caused by rotation of the surgical tools. The diameter of the guide portion 45 of the punch 1a corresponds to the inner diameter of the guide channel 21a, 21b. That is, the guide surface 47 of the guide portion 45 can cooperate with the mating guide surface of the guide channel 21a, 21b of the template 20. When properly positioned in the patient's mouth, the axis of the guide channel 21a, 21b coincides with the axis of the implant hole to be drilled.

When the punch 1a is inserted in the guide channel 21a, 21b of the template 20, such that the guide portion 45 is in contact with the guide channel 21a, 21b, the longitudinal axis 5 of the punch 1a coincides with the axis of the guide channel 21a, 21b and as such, with the axis of the implant hole to be drilled. The close fit between the guide portion 45 and the guide channel 21a, 21b prevents the mucosa punch 1a, from deviating and allows the mucosa 3 on the site of the prospective implant to be removed precisely. The truncated cone shape of functional element 10 makes it easier to insert the tool 1 into the guide channel 21a, 21b.

Visual markers 50a, 50b, 50c act as depth indicator markings. By aligning these with the upper surface of the template 20, i.e. the surface furthest from the jaw bone, the user is informed of the depth of a reference point on the functional element 10 of the tool 1, e.g. the tip of the cutting edge 15. In the present example, visual marker 50c is aligned with the upper surface of the template 20. This informs the user that the cutting edge 15 of the punch 1a is resting on the surface of mucosa 3. By pressing the punch downwards until visual marker 50b is aligned with this surface the user knows that the cutting edge 15 will have penetrated the soft tissue 3 to a predetermined depth.

As the visual markers 50a, 50b, 50c are formed by grooves 55, the visibility of the markers 50a, 50b, 50c is not degraded over time due to abrasion by channel 21a, 21b. In addition, the finite nature of grooves 55 ensures that at every axial location of the guide portion 45, at least a segment 65 of guide surface 47 is present to ensure smooth guidance of the tool 1a.

Figure 5:
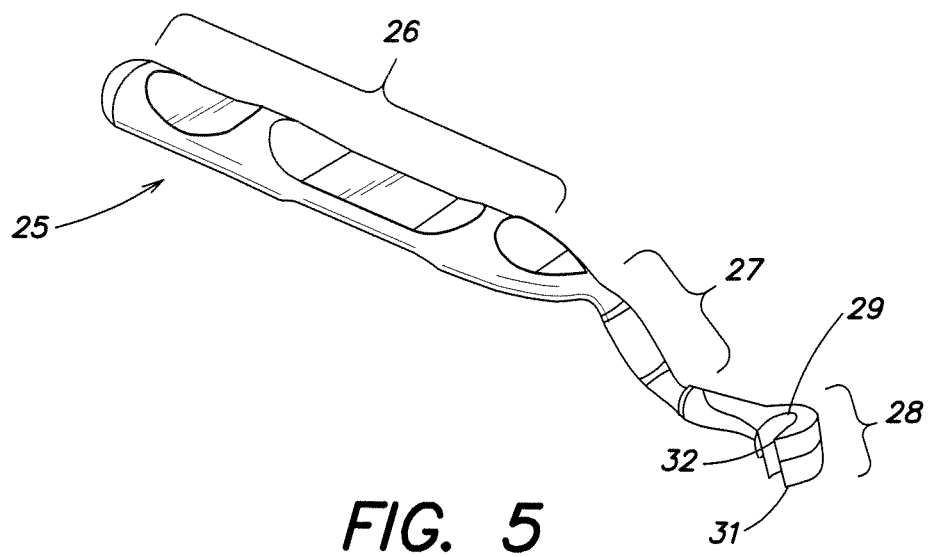
FIG. 5 shows a C-handle which can be used with tools in accordance with the present invention.

In order to enable template 20 to be used with tools having a narrower guide portion 45, guide collars can be used to modify the diameter of guide channel 21a, 21b. An example of such a collar is shown in FIG. 5. This component is called a C-handle 25. It consists of a handle section 26, for gripping by the user, neck section 27 and head section 28. Head section 28 is "C" shaped and defines a central three sided channel 29. Head portion 28 has a lower section 31, which has an outer diameter corresponding to the inner diameter of guide channel 21a, 21b. Upper section 32 has a slightly larger outer diameter such that this cannot fit within guide channel 21a, 21b and instead abuts the upper surface of the template 20. The C-handle 25 can therefore be used to reduce the diameter of the guide channel 21a, 21b and thus enables the template 20 to provide accurate guidance to tools having guide portions 45 of differing diameters. It is also possible for a similar guide collar to be provided in which the head portion 28 comprises a closed channel.

FIGS. 6a, 6b, and 6c each depict a guide portion 45a, 45b, and 45c, respectively, with two markers 50d, 50e in the form of grooves 55 and a cross section along line II-II, line and line IV-IV, respectively. FIG. 6a shows a guide portion 45a with seven grooves 55 per visual marker 50 and seven remaining segments 65 of the guide portion 45a in between the grooves 55, as can easily be seen in cross section II. FIG. 6b shows a guide portion 45b with a smaller radius r as compared to the guide portion 45a in FIG. 6a. Cross section III reveals six grooves 55 in one marker 50. FIG. 6c shows a guide portion 45c with an even smaller radius r and only five grooves 55 in one marker 50. These figures demonstrate that the number of grooves 55 or other recesses can be altered depending on the diameter r of the guide portion 45. Alternatively the number of grooves 55 could be kept constant but the length 56 of these grooves shortened. Many design variations are possible which meet the dual requirements of providing adequately visible recesses whilst maintaining enough guide surface to provide smooth guidance. Cross section IV-IV shows, as an example, possible relative dimensions: the grooves 55 have a length 56, which is about 1.02 mm, and a depth 75, which is about 0.1 mm; whereas the remaining segments 65 have a length 66 in circumferential direction of 0.64 mm. This gives a ratio between groove and segment length of approximately 1.6.

The axial widths 70 of the grooves 55 shown in FIGS. 6a and 6b are uniform. However, FIG. 6c shows an embodiment in which different visual markers have grooves of differing axial widths 70.

Figure 7A:
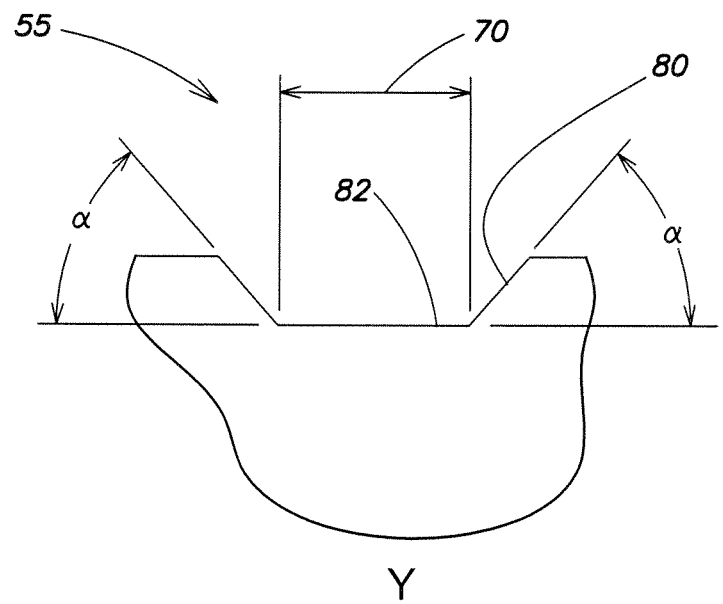
FIGS. 7A and 7B show details from FIG. 6A and FIG. 6C respectively, FIG. 7A showing detail Y from FIG. 6A and FIG. 7B showing detail Z from FIG. 6C.
Figure 7B:
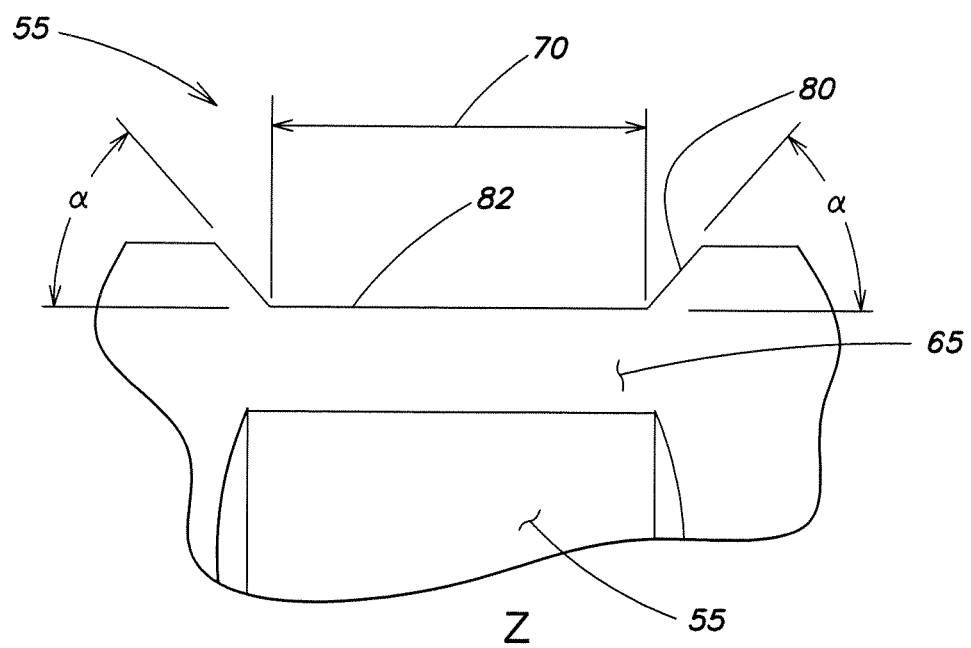

FIGS. 7a and 7b show details Y and Z of FIG. 6a or 6c respectively, which depict a groove 55 with a width 70 in axial direction. The sides 80 of both grooves are bevelled at an angle α, which in this embodiment is 45°. The embodiment of the guide portion 45 shown in FIG. 6c and detail Z has a larger groove width 70 than the groove width 70 in the embodiment shown in FIG. 6a and detail Y.

In these preferred embodiments, grooves 55 are formed with a planar ground 82. In order to increase the visibility of the visual markers, the grounds 82 of the grooves 55 may contain a mark. Preferably, the mark is made by laser-marking.

Figure 8:
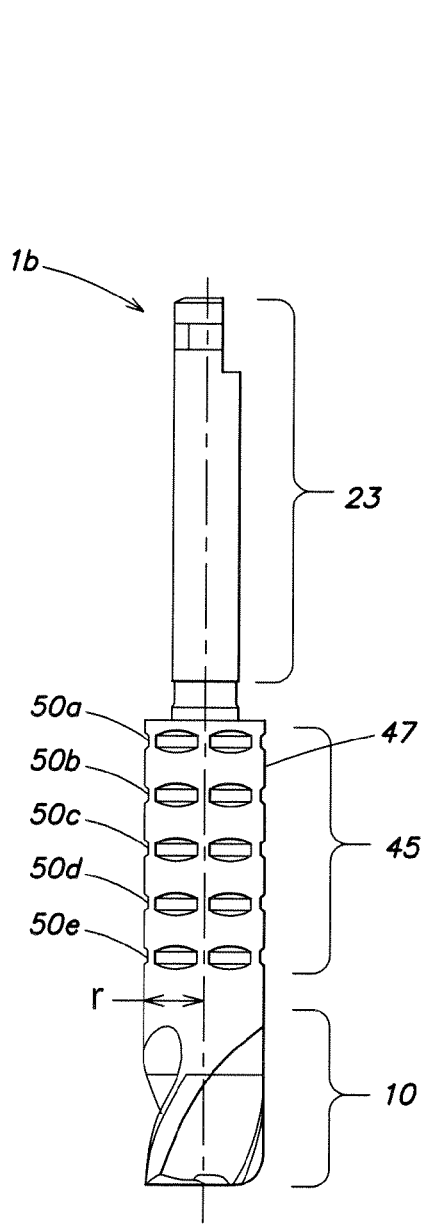
FIG. 8 shows a milling cutter in accordance with the present invention.
Figure 9:
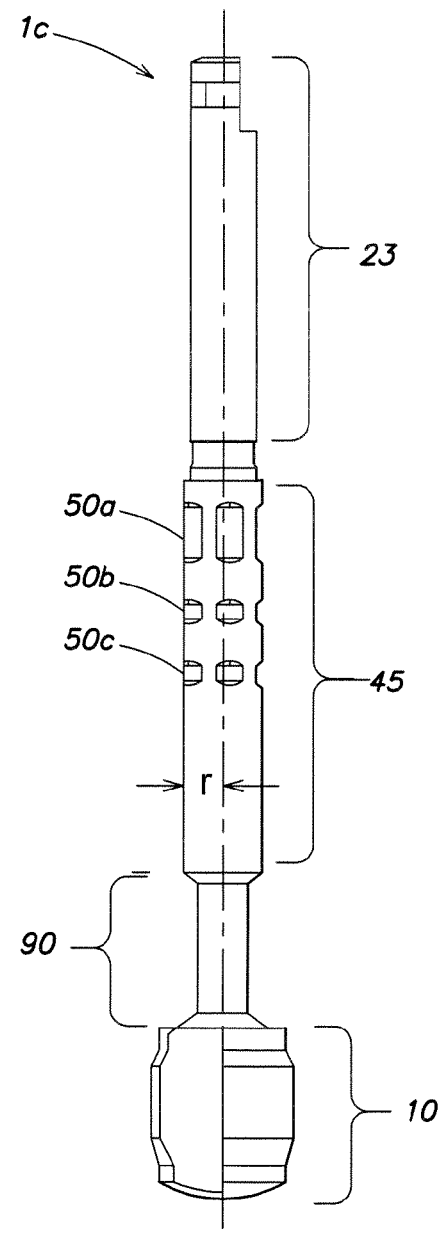
FIG. 9 shows a tap in accordance with the present invention.

FIGS. 8 and 9 show examples of further surgical tools in accordance with the present invention.

FIG. 8 shows a milling cutter 1b. This tool is used to level the bone surface prior to drilling. Like the punch 1a of FIG. 1, milling cutter 1b comprises a functional element 10, a guide portion 45 and a shank 23. In this embodiment functional element 10 does not form a truncated cone but has an outer radius r equivalent to the radius r of guide portion 45. Guide portion 45 comprises a plurality of visual markers 50a-50e, each consisting of a number of finite grooves 55 of the type described above. These grooves 55 are separated from one another by sections of the guide portion 45 having radius r. This ensure that at every axial location of the guide portion 45 there exist portions of guide surface 47 which can cooperate with a guide channel to control the orientation of the milling cutter 1b. In this example, grounds 82 of the grooves 55 have been lasermarked to increase the visibility of the markers 50a-50e.

FIG. 9 shows a tap 1c (threads not shown). Once again this comprises a functional element 10, a guide portion 45 and a shank 23. Visual markers 50a-50c are located on the guide portion 45 and comprise a series of finite grooves 55 which have been lasermarked. As can be seen, the outer radius r of the guide portion 45 of tap 1c is less than the radius r of guide portion 45 of milling cutter 1b. In order for the tap 1c to be used in combination with the same template as milling cutter 1b, a guide collar such as the C-Handle 25 shown in FIG. 5 must be used. The open channel 29 of C-handle 25 enables the tap 1c to be inserted into the C-handle 25 despite the size of functional element 10, which has a larger diameter than the guide portion 45. Tap 1c comprises a neck portion 90 located between functional element 10 and guide portion 45 in order to ease the insertion of the tap 1c into the C-handle 25, however this neck portion 90 is not essential.

The visual markers 50 of milling cutter 1b and tap 1c are positioned on the guide portions 45 at defined axial locations which enable these to be used, in combination with the upper surface of template 20 or C-handle 25, to indicate the depth of functional element 10. Due to the different functions of the tools 1b, 1c the visual markers 50 are positioned differently. Milling cutter 1b is used prior to drilling in order to level the bone surface. This is therefore used close to the surface of the alveolar bone 2 and hence visual markers 50 are located close to the functional element 10. On the other hand, tap 1c is used to create threads on the inner walls of the bone cavity. Hence, this tool is inserted deeper into the alveolar bone 2, e.g. 8-14 mm. The visual markers 50 are therefore positioned further away from the functional element 10. In each case, guide portion 45 is positioned and dimensioned such that sliding contact can be maintained with the guide element at all operative axial positions of the tool.

Further embodiments which fall within the scope of the claims are conceivable. The marks of the different sets of grooves may have a different colour. In addition the visual markers could consist of recesses having different shapes. These can be intended to provide depth information, tool diameter, tool function etc.

The invention claimed is:

1. Surgical tool for use in guided surgery with a longitudinal axis comprising:
    a functional element at a distal end of the tool,
    a shank on the opposite end of the tool, and
    a cylindrical guide portion having an outer radius r which defines a guide surface for cooperation with a guide element, the guide portion being located on the longitudinal axis between the functional element and the shank and having a plurality of markers lying in different axial planes,
    each marker comprising a plurality of recesses located in the same axial plane and having the same distance to the distal end of the tool, forming a set, said recesses being finite in the circumferential direction and separated from each other by sections of the guide surface such that, at the axial location of the marker, sections of the guide surface are maintained,
    wherein the plurality of recesses in each marker are positioned in such a way that at least one recess is visible from any viewing angle about the longitudinal axis.

2. Surgical tool according to claim 1, wherein said at least one marker is a visual marker.

3. Surgical tool according to claim 2, wherein the at least one recess contains a mark.

4. Surgical tool according to claim 3, wherein said mark is made by laser-marking.

5. Surgical tool according to claim 3, wherein the mark lies completely within the distance r from the longitudinal axis of the surgical.

6. Surgical tool according to claim 2, wherein said at least one recess is a finite groove.

7. Surgical tool according to claim 6, wherein said groove comprises a ground.

8. Surgical tool according to claim 7, wherein the at least one groove contains a mark on the ground of the groove.

9. Surgical tool according to claim 7, wherein the ground is planar.

10. Surgical tool according to claim 2, wherein the axial width of the at least one recess is between 0.4 and 2.5 mm.

11. Surgical tool according to claim 10, wherein the axial width is between 0.5 and 2.0 mm.

12. Surgical tool according to claim 2, wherein the tool is a dental tool.

13. Surgical tool according to claim 12, wherein the dental tool comprises a punch, a milling cutter, a tap, a profile drill, a drill or a transfer piece.

14. Surgical tool according to claim 1, wherein the number of recesses per set is 2 to 9.

15. Surgical tool according to claim 1, wherein the ratio of the combined length of the recesses in a set to the combined length of the remaining sections of the guide surface in the same axial plane is between 1 and 3.

16. Surgical tool according to claim 15, wherein the ratio is between 1.4 and 2.7.

17. Surgical tool according to claim 1, wherein the plurality is 2 to 5.

18. Kit comprising a surgical tool and a guide element, the surgical tool comprising
   a longitudinal axis,
   a functional element at a distal end of the tool,
   a shank on the opposite end of the tool, and
   a cylindrical guide portion having an outer radius r which defines a guide surface for cooperation with the guide element, the guide portion being located on the longitudinal axis between the functional element and the shank and having at least one marker,
   the at least one marker comprising a plurality of recesses, said plurality of recesses being finite in the circumferential direction such that, at the axial location of the recess, a section of the guide surface is maintained,
   wherein the plurality of recesses in each marker are positioned in such a way that at least one recess is visible from any viewing angle about the longitudinal axis.

19. Kit as claimed in claim 18 wherein the at least one marker of the surgical tool is arranged to indicate, in cooperation with the guide element, the depth of the functional element of the tool.

* * * * *